US007153315B2

(12) United States Patent
Miller

(10) Patent No.: US 7,153,315 B2
(45) Date of Patent: Dec. 26, 2006

(54) CATHETER BALLOON WITH ULTRASONIC MICROSCALPEL BLADES

(75) Inventor: Paul James Miller, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 426 days.

(21) Appl. No.: 10/167,214

(22) Filed: Jun. 11, 2002

(65) Prior Publication Data

US 2003/0229370 A1    Dec. 11, 2003

(51) Int. Cl.
*A61B 17/22* (2006.01)

(52) U.S. Cl. ........................................ 606/159

(58) Field of Classification Search ............... 600/207, 600/471; 604/22, 96.01, 508; 606/159, 606/167, 169, 192, 193, 194
See application file for complete search history.

(56) References Cited

U.S. PATENT DOCUMENTS

| 4,273,128 A | 6/1981 | Lary .......................... 128/305 |
| 4,838,853 A | 6/1989 | Parisi ........................... 604/22 |
| 4,860,744 A | 8/1989 | Johnson et al. .......... 128/303.1 |
| 5,000,185 A * | 3/1991 | Yock ............................ 600/459 |
| 5,046,503 A | 9/1991 | Schneiderman ............. 128/692 |
| 5,057,107 A | 10/1991 | Parins et al. ................... 606/48 |
| 5,059,203 A | 10/1991 | Husted ......................... 606/159 |
| 5,064,994 A | 11/1991 | Urban .......................... 219/233 |
| 5,085,662 A * | 2/1992 | Willard ........................ 606/159 |
| 5,181,920 A | 1/1993 | Mueller et al. .............. 606/159 |
| 5,196,024 A | 3/1993 | Barath ........................ 606/159 |
| 5,243,997 A | 9/1993 | Uflacker et al. ............. 128/772 |
| 5,320,634 A | 6/1994 | Vigil et al. ................... 606/159 |
| 5,336,234 A | 8/1994 | Vigil et al. ................... 606/159 |
| 5,474,530 A | 12/1995 | Passafaro et al. ............. 604/22 |
| 5,549,604 A | 8/1996 | Sutcu et al. ................... 606/45 |
| 5,609,606 A | 3/1997 | O'Boyle ...................... 606/194 |
| 5,611,807 A | 3/1997 | O'Boyle ...................... 606/169 |
| 5,616,149 A | 4/1997 | Barath ........................ 606/159 |
| 5,695,510 A | 12/1997 | Hood .......................... 606/169 |
| 5,728,089 A * | 3/1998 | Lal et al. ........................ 606/1 |
| 5,876,369 A | 3/1999 | Houser ......................... 604/22 |
| 5,904,679 A | 5/1999 | Clayman ..................... 606/39 |
| 5,916,192 A | 6/1999 | Nita et al. ..................... 604/22 |
| 5,941,869 A * | 8/1999 | Patterson et al. ........... 604/508 |
| 5,944,717 A | 8/1999 | Lee et al. ...................... 606/48 |
| 5,980,518 A | 11/1999 | Carr et al. ..................... 606/45 |
| 6,041,686 A | 3/2000 | Lihl et al. ..................... 83/628 |
| 6,083,232 A | 7/2000 | Cox ............................. 606/128 |

(Continued)

FOREIGN PATENT DOCUMENTS

EP    0623315 A1    1/1994

(Continued)

OTHER PUBLICATIONS

PCT International Search Report, PCT/US03/16141 (5 pages) [included with application, but not cited by applicant].*

*Primary Examiner*—Anhtuan T. Nguyen
*Assistant Examiner*—Tuan V. Nguyen
(74) *Attorney, Agent, or Firm*—Vidas, Arrett, Steinkraus

(57) ABSTRACT

The present invention provides a catheter balloon, and balloon catheter incorporating the catheter balloon, useful in medical dilation procedures. The catheter balloon includes at least one microscalpel operatively disposed on an outer surface thereof. The microscalpel may advantageously be operatively disposed relative to a power source so as to be controllably activatable. Also provided are methods of making the inventive balloon and/or catheter as well as methods of using the inventive catheter in a dilation/incising treatment.

16 Claims, 3 Drawing Sheets

| U.S. PATENT DOCUMENTS | | | | FOREIGN PATENT DOCUMENTS | | |
|---|---|---|---|---|---|---|
| 6,287,272 B1 | 9/2001 | Brisken et al. | 604/22 | EP | 0820728 A2 | 1/1998 |
| 6,306,151 B1 * | 10/2001 | Lary | 606/159 | EP | 1169970 A1 | 7/2001 |
| 6,383,183 B1 | 5/2002 | Sekino et al. | 606/34 | | | |
| 6,464,660 B1 * | 10/2002 | Brisken et al. | 604/22 | * cited by examiner | | |

CATHETER BALLOON WITH ULTRASONIC MICROSCALPEL BLADES

FIELD OF THE INVENTION

The present invention pertains generally to catheter balloons useful in medical dilation. More specifically, the present invention relates to catheter balloons having microscalpel blades operatively disposed relative thereto, which blades may advantageously be provided with controllable ultrasonic energy, if desired.

BACKGROUND OF THE INVENTION

Angioplasty is a widely utilized therapeutic treatment in which obstructed intraluminal spaces are reopened or dilated. In a typical procedure, a catheter comprising an inflatable member, such as a balloon, is inserted percutaneously into the patient's luminal passage, such as an arterial passage. Once inserted, the balloon is advanced to the desired treatment site, where the balloon may be inflated to dilate the luminal passage.

Although vascular angioplasty is a widely utilized and largely successful procedure, the procedure can cause collateral trauma to the vessel wall. That is, in order to dilate the area of obstruction, pressure is typically applied, which pressure is realized at the vessel wall. The applied pressure can result in the stretching, or irregular intimal tearing, of layers of the vessel wall, which in turn, can result in restenosis of the treatment site. Any such restenosis that occurs may require further treatment, an outcome that would desirably be avoided.

In order to avoid, or minimize the possibility of such an outcome, devices have been developed that purport to reduce the pressure applied, as well as any potentially resulting collateral damage to the vessel wall. For example, balloons incorporating cutting blades have been provided in conjunction with angioplasty catheters. These cutting balloons, when dilated within a stenosis, provide regular, controlled incisions in the stenosis. It is thought that, unlike irregular intimal tearing, these regular incisions can act to disperse the pressure that otherwise would be realized outwardly at the vessel wall radially about the treatment site, thereby reducing damage to the vessel wall. Although such cutting balloon angioplasty procedures are widely utilized and largely successful procedures, improvements to the same could yet be made.

For example, in some applications, it may be desirable to enhance the precision of the incisions that can be made in a stenosis. Enhanced precision would be advantageous, for example, as it is believed that the sharper and cleaner the cuts provided in a stenosis, the greater the reduction in restenotic response that will be seen. Enhanced precision in the depth of the incision provided would be advantageous as well, inasmuch as such depth precision currently can be difficult to attain, in particular when such cutting elements are provided in conjunction with a compliant balloon.

SUMMARY OF THE INVENTION

The present invention is generally directed to cutting balloons having at least one microscalpel blade operatively disposed relative thereto. In certain embodiments, the microscalpel may be operatively disposed relative to a power source, preferably a source of ultrasonic energy. Advantageously, the ultrasonic microscalpels, because of their small size and/or the provision of ultrasonic energy thereto, are capable of creating much sharper and cleaner incisions in a stenosis than conventional cutting blades. The ability to selectively activate, deactivate, pulse, or otherwise vary, the source of energy further enhances the cutting precision of the microscalpels and thus, balloon. As a result, the inventive cutting balloons can be used to incise stenosis at lower dilatation pressures, or to incise stenosis that are difficult to incise utilizing other conventional cutting balloons. Trauma to the vessel wall, as well as any subsequent restenosis that can result therefrom, can thus be reduced.

In one aspect then, the present invention provides a dilatation balloon and balloon catheter. Generally, the dilation balloon includes a balloon body having an outer surface and at least one microscalpel operatively disposed on the outer surface of the balloon body. The microscalpel may advantageously be activatable by a source of power, preferable a source of ultrasonic energy. A balloon catheter embodying features of the present invention generally includes the inventive balloon further having an interior, as well as an elongated catheter shaft having a proximal end, a distal end and an inflation lumen of the catheter shaft extending through at least a portion thereof. The balloon is mounted near the distal end of the catheter shaft so that the inflation lumen is in fluid communication with the interior of the balloon.

Inasmuch as the present invention is based, at least in part, upon the recognition of the advantages that may be attained by the provision of microscalpels smaller than conventional cutting elements on the surface of a cutting balloon, and the further advantages that can be seen when the microscalpels are ultrasonically activatable, the type of balloon and/or catheter, the materials(s) used to manufacture the same, and the configuration of the same once assembled, is not critical. Rather, the inventive cutting balloon catheters can be provided by utilizing any material, or combination of materials, may be coated or uncoated, cross-linked or uncrosslinked, etc., so long as the balloon has provided thereon at least one microscalpel. In fact, and due at least in part to the fact that microscalpels can be much sharper than conventional cutting elements, a broader range of materials is suitable for use in the inventive cutting balloon than is appropriate for use in conventional cutting balloons.

In another aspect, the present invention provides a method for producing a balloon catheter. Generally speaking, the method involves the steps of providing a cutting dilation balloon, having an interior and an outer surface having operatively disposed relative thereto at least one microscalpel. In certain embodiments, the microscalpel is desirably controllably ultrasonically activatable. A catheter shaft is also provided having a distal end, a proximal end, and an inflation lumen extending through at least a portion thereof. The cutting balloon is then mounted on the catheter so that the inflation lumen of the catheter shaft is in fluid communication with the balloon interior.

The inventive balloon and balloon catheter can be utilized to dilate a stenosis while doing so at a generally lower dilatation pressure and/or in manner that results in less trauma to the vessel wall. As a result, a reduction in any restenosis that might otherwise occur can be seen. Thus, in yet another aspect of the present invention, a method for incising and/or dilating a stenosis is provided. Generally, the method involves providing balloon catheter having a catheter shaft having a lumen in fluid communication with the interior of a cutting balloon, the cutting balloon having at least one microscalpel mounted thereon. If desired, the microscalpel may advantageously be operatively disposed relative to a controllable energy source, such as a source of ultrasonic energy. The catheter is inserted into the bodily lumen and directed to the site to be dilated. The balloon is then inflated so that at least one microscalpel at least partially incises the stenosis. The microscalpel may be controllably activated with ultrasonic energy, if an energy source is provided and it's use is desirable, to further enhance the precision of the incisions made.

These and other features and advantages of the present invention will be apparent in the following detailed description of the preferred embodiments when read in conjunction with the accompanying drawings, in which like reference numerals are used to identify the same or similar parts in the several views.

BRIEF DESCRIPTION OF THE DRAWINGS

The accompanying drawings, which are incorporated in and constitute a part of this application, illustrate several aspects of the invention and together with description of the illustrated embodiments serve to explain the principles of the invention. A brief description of the drawings is as follows.

DETAILED DESCRIPTION

Figure 1:
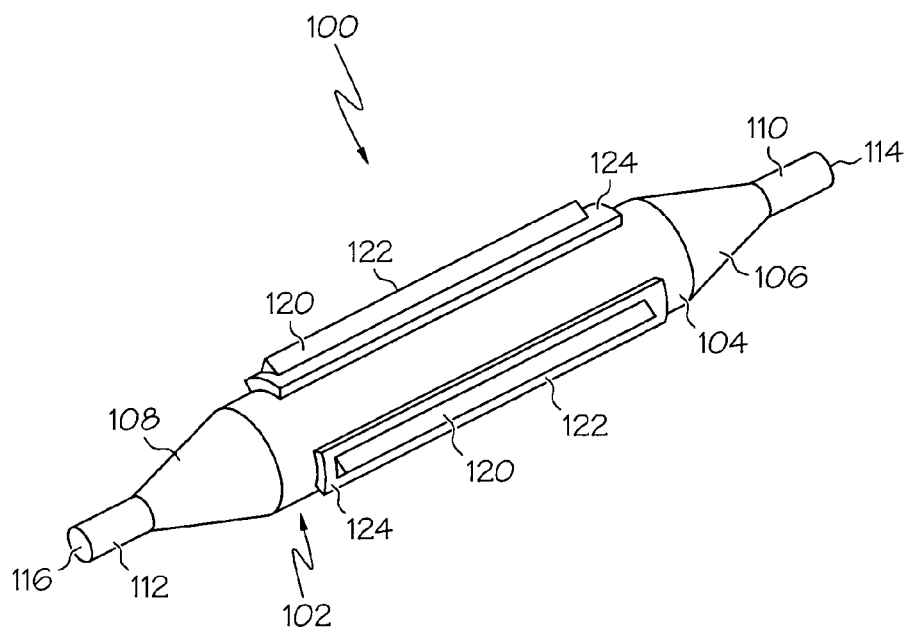
FIG. 1 is a perspective view of a cutting balloon embodying features of the present invention and showing in particular a plurality of microscalpel cutting blades operatively disposed relative thereto.

The embodiments of the present invention described below are not intended to be exhaustive or to limit the invention to the particular embodiments disclosed in the following detailed description. Rather, the embodiments are described so that others skilled in the art can understand the principles and practices of the present invention.

The present invention provides a cutting balloon, and dilation catheter incorporating the same, wherein the cutting balloon has at least one microscalpel blade operatively disposed relative thereto. Advantageously, a source of energy, preferably ultrasonic energy, may be operatively disposed relative to the microscalpel. The inventive cutting balloon, incorporating such microscalpels, or energizable microscalpels, and when provided in conjunction with an angioplasty catheter, can provide advantages not attainable, or for the enhancement of advantages attainable, from a conventional cutting balloon catheter.

Generally speaking, cutting balloons embodying features of the present invention include a balloon having provided operatively disposed thereto at least one microscalpel blade which microscalpel may be further advantageously operatively disposed relative to a power source. The present invention further generally provides a cutting balloon catheter further including, in addition to the inventive cutting balloon, a catheter shaft in fluid communication with the cutting balloon.

Inasmuch as the invention is based at least in part upon the discovery that microscalpels that comprise a much smaller cutting surface or edge than conventional cutting elements can be provided in connection with an angioplasty balloon, that these microscalpels can advantageously be supplied with energy, and further, the advantages that could be obtained by using such device in a dilation procedure, the particular type of balloon or catheter shaft utilized in the inventive balloon and/or balloon catheter are not critical. Rather, any type of catheter shaft and/or balloon, arranged in any configuration, can be employed to provide the inventive balloon or device.

For example, the cutting balloon may be any balloon, of any size or geometry, made of any material or combination of materials, by any method, coated or uncoated, and may be crosslinked or uncrosslinked, having at least one microscalpel blade operatively disposed in connection therewith.

In fact, and due at least in part to the fact that microscalpels can be much sharper than conventional cutting elements, a broader range of materials is suitable for use in the inventive cutting balloon than is appropriate for use in conventional cutting balloons. For example, and in addition to materials conventionally used in cutting balloons, Pebax® (a PolyEther Block Amide), polyurethanes, latex, polyethylene, Hytrel® (a thermoplastic polyester elastomer) and ionomers can be utilized in the formation of a cutting balloon embodying features of the present invention.

Likewise, the catheter shaft may be any of those used to provide any of the various designs for balloon catheters known in the art. Examples include over-the-wire catheters, single operator or rapid exchange catheters, to name a few. Additionally, the catheter shaft can be made from any material, by any method, may be coated or uncoated. Further, the catheter shaft, including any components thereof, can have the dimensions of any conventional dilatation catheter, and inner and outer tubular members as may be incorporated into the same.

As mentioned above, the inventive cutting balloon includes at least one microscalpel blade. As used herein, the phrase "microscalpel blade" or term "microscalpel" is meant to indicate any cutting blade, surface, element, edge or the like, that comprise a cutting edge or surface that is generally smaller and/or sharper than any conventional cutting blade used in conjunction with angioplasty balloons. Generally speaking, microscalpel blades embodying features of the present invention have a cutting surface that is advantageously at least 2 times sharper than any associated with any conventional cutting blade, preferably at least 5 times sharper, and most optimally at least 10 times sharper than cutting edges of conventional cutting blades.

One way of quantifying sharpness is via measurement of the radius of curvature of the cutting edge or surface. For example, one known conventional cutting blade used in conjunction with angioplasty balloons is made from stainless steel and has a radius of curvature of greater than about 100 nm. A microscalpel blade embodying features of the present invention would thus be sharper than this conventional cutting element by including a cutting edge having a radius of curvature of less than about 100 nm, advantageously less than about 50 nm, more advantageously less than about 20 nm and most optimally, less than about 10 nm.

The microscalpel blades may be formed from any material, or combination of materials, capable of being manufactured to form a cutting blade includes a cutting surface that is smaller and/or sharper than a conventional cutting blade. One example of a material suitable for use in the production of such microscalpels is a crystalline material, including either monocrystalline or polycrystalline materials. Such materials are easily manufactured into small structures, while yet providing structures having sufficient strength so as to be useful as a cutting blade. Examples of such materials include, but are not limited to, silicon, quartz sapphire, diamond (such as diamond-like-carbon), and the like.

The microscalpel cutting blades may further be formed from a combination of materials. The utilization of a combination of materials may be desirable, for example, when the base material is capable of being manufactured to have the desired sharper cutting surface relative to a conventional cutting blade, but wherein the resulting microscalpel may lack the desired strength for use in this capacity. The microscalpel cutting blades may thus be formed from any material, including noncrystalline materials such as glasses, metals, polymers etc, and have provided in combination therewith an additional material or materials to provide the microscalpel with the desired strength or with a desired edge having the desired radius of curvature.

The microscalpel cutting blades may optionally be coated. If desired, any coating, applied in any thickness and by any method, for any desired purpose, may be used, so long it is suitable for use in conjunction with a medical device. Coatings may desirably be provided to, e.g., enhance lubricity, impart radioopacity, to deliver therapeutic agents therefrom, etc. A coating may further be applied to enhance the strength, or to otherwise protect, the microscalpel cutting blades. Strength enhancing coatings or thin films include, but are not limited to, silicon dioxide, silicon nitride, titanium diboride, diamond like carbon, and silicon carbide.

The method used to form the microscalpel cutting blades is not critical. Rather, the microscalpel cutting blades may be formed by any method of manufacture appropriate for the chosen material, so long as the microscalpels produced by such a method have a sharper cutting edge or surface than conventional cutting elements. Such methods include, of course, those methods currently utilized to produce conventional cutting elements. Examples of such methods include, but are not limited to, oxidation sharpening processes or mechanical techniques, such as mechanical cleavage.

Advantageously, when the microscalpels are desirably formed from crystalline materials, the microscalpel blades may be formed by methods commonly utilized to manufacture semiconductor devices. Such techniques are capable of producing large volumes of microscalpel blades inexpensively and further capable of producing incredibly small microscalpels having intricate features, if desired. Exemplary techniques include etching, such as anisotropic or isotropic etching techniques, further including ion etching (RIE), ion beam milling or chemical etching via the application of chemical agents.

The provision of energy to the microscalpel blades can provide further advantages to the inventive cutting balloon and catheter. For example, the application of energy to the microscalpel cutting blades can further reduce the pressure required to incise a stenosis, i.e. beyond the reduction already provided by the enhanced sharpness of the microscalpels relative to conventional cutting elements. Advantageously, the energy provided to the microscalpel cutting blades may be controllable, so that the energy may be turned on, off, pulsed, or otherwise varied in type, strength, etc., further enhancing the control and precision that may be exercised over incising a stenosis using the inventive cutting balloon and catheter. Thus, the microscalpel blades are desirably and advantageously operatively disposed relative to a power source that supplies energy, such as thermal, RF, electric, or oscillatory energy, to the microscalpels. Preferably, oscillatory energy, more preferably, ultrasonic energy, is provided by a power source to the microscalpel blades.

Energy may be supplied to the microscalpel cutting blades by any method, using any componentry, arranged in any configuration, so long as however supplied, the energy is capable of at least partially activating at least a portion of at least one microscalpel blade. Methods of providing energy from a source to a remote area are well known to those of ordinary skill in the electrical engineering arts, and any of these may be used.

For exemplary purposes only then, one such configuration might have the power source provided as a component separate from the balloon catheter and connected to the microscalpels via one or more conductors capable of conducting or transmitting the energy provided by the power source. Any such conductor(s) may be connected directly to the microscalpel blades, or may be operatively disposed to a transducer that is in turn operatively disposed relative to the microscalpel blades. If the conductor(s) are desirably connected directly to the microscalpels, the conductors themselves are desirably operatively disposed relative to a transducer.

The transducer is desirably provided in any configuration wherein the transducer is capable of supplying energy provided by the power source to the microscalpel blades in order to activate at least a portion of at least one microscalpel. For example, the transducer may be provided in connection with the balloon and operatively disposed relative to the microscalpel blades. Indeed, microscalpel cutting blades can be attached to the transducer which is in turn, attached to a surface of the cutting balloon, if desired. The transducer may also be an integral part of the microscalpel cutting blades, i.e., as would be the case if a thin film transducer were formed directly on at least a portion of a surface of at least one microscalpel blade. Such transducer structures are generally well-known and comprise multilayer thin film structures including piezoelectric layers and contact layers.

Clearly, given the above, the type of balloon and catheter to which the inventive concept, the provision of ultrasonically activatable microscapels in connection therewith, is not particularly limited and such a construction is not intended. For illustration and exemplary purposes only, then the following figures and description thereof is provided.

Referring now to FIG. 1, there is illustrated an exemplary cutting balloon 100 embodying features of the present invention. Generally, cutting balloon 100 comprises a substantially cylindrical body 102 having an outer surface 104, a distal cone section 106, a proximal cone section 108, a distal waist section 110 and proximal waist section 112. Distal waist section 110 and proximal waist section 112 include openings 114 and 116, respectively, for operatively positioning balloon 100 with respect to a catheter shaft (not shown). A plurality of microscalpel blades 120 are disposed on outer surface 104 of body 102. It is noted that the representation of FIG. 1 may or may not be to scale, given the nature of microscalpel blades 120.

Microscalpel blades 120 include an edge 122 having a radius of curvature less than that of conventional cutting elements, i.e., less than about 100 nm. Although microscalpel blades 120 are shown in FIG. 1 having a certain shape and configuration, these are not critical, and microscalpel blades 120 can be provided in any shape and configuration so long as at least a portion of one edge 122 of microscalpel cutting blades 120 has a radius of curvature smaller than that of conventional cutting elements provided in connection with angioplasty balloons.

For example, although FIG. 1 illustrates microscalpel blades 120 as a single contiguous structure extending in a substantially parallel fashion along substantially the entirety of the longitudinal axis of balloon 100, this configuration is not required. Rather, microscalpel blades 120 can be provided in connection with outer surface 104 of balloon body 102 in any configuration, such as in the form of individual units, each substantially shorter in length than the body 102 of balloon 100, and may be provided in, e.g., a helical configuration, in relation to the outer surface 104 of balloon body 102. Microscalpel blades 120 may also have disruptions, such as serrations provided on edge 122 thereof. Finally, although two microscalpel blades 120 are illustrated in FIG. 1, any number of microscalpel blades 120 may be provided on the surface 104 of balloon body 102.

Microscalpels 120 are mounted to the outer surface 104 of the balloon body 102 via mounting elements 124. Mounting elements 124 may be comprised of any material capable of adhering microscalpels 120 to the outer surface 104 of balloon body 102. For example, mounting elements 124 may comprise an elastomeric polymer, such as polyurethane, or may comprise an effective amount of an adhesive, such as a cyanoacrylate or polyurethane adhesive. Although illustrated as such in FIG. 1, microscalpel blades 120 need not be indirectly adhered to the outer surface 104 of balloon body 102 via such mounting elements 124. Rather, microscalpel blades 120 can be formed to be an integral component of balloon 100 during the balloon molding process.

Figure 2:
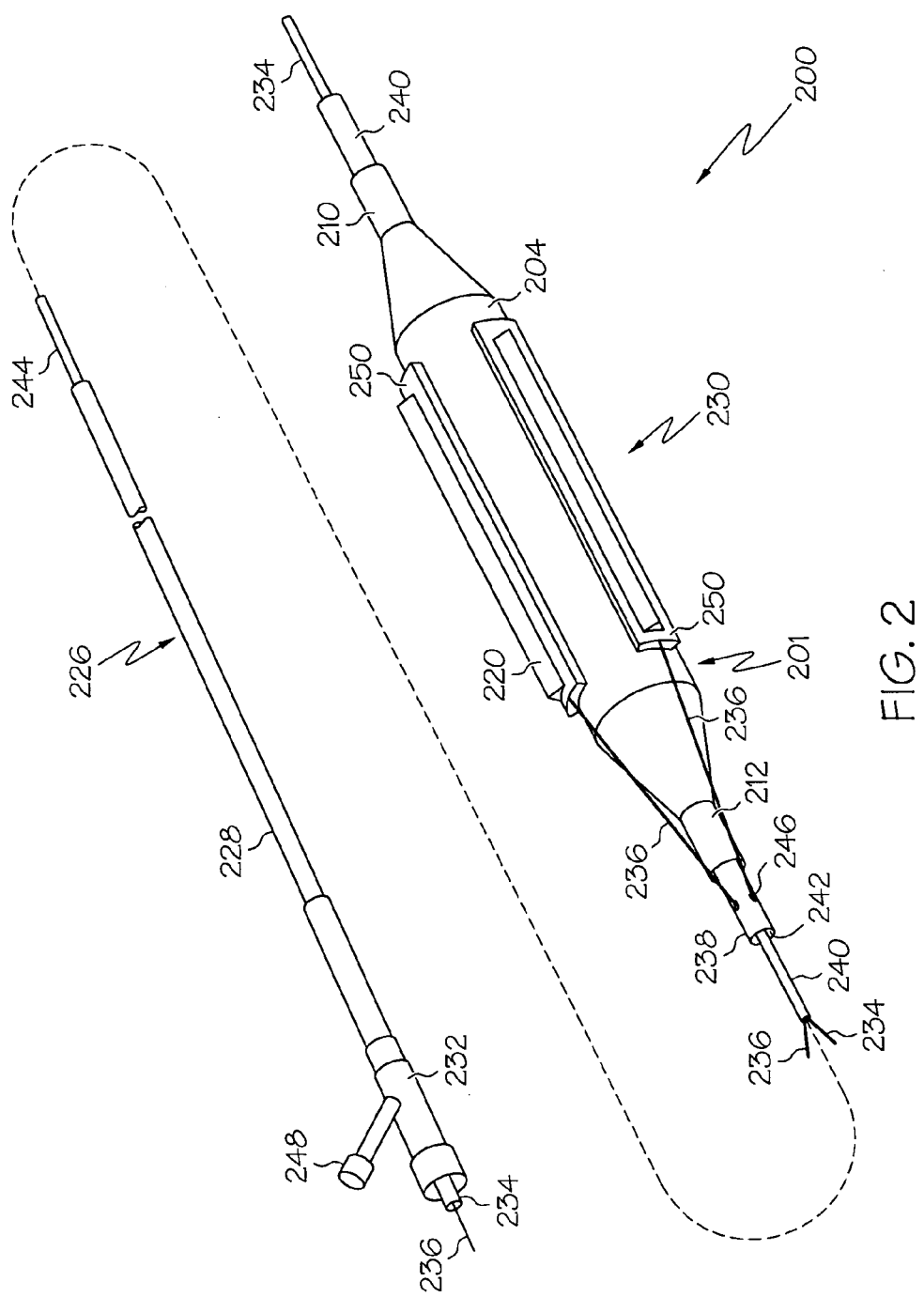
FIG. 2 is a perspective view of a balloon catheter embodying features of the present invention wherein a plurality of microscalpel cutting blades are operatively disposed relative to the balloon and the microscalpel cutting blades are further operatively disposed relative to a power source so as to be controllably activatable.

Referring now to FIG. 2, a balloon catheter embodying features of the present invention, generally designated number 200, is illustrated. Balloon catheter 200 generally includes an elongated catheter shaft 226, having proximal section 228 and distal section 230, balloon 201, microscalpels 220, transducers 250 and conductors 236. Cutting balloon 201 is disposed on the distal section 230 of catheter shaft 226, and manifold 232 is mounted on proximal section 228 of shaft 226 to permit controllable sliding over guidewire 234 and conductor 236, and for fluid introduction within shaft 226. Conductors 236 have a proximal end operatively disposed relative to a power source (not shown), and a distal end operatively disposed relative to transducers 250, which transducers 250 are, in turn, operatively disposed to microscalpels 220. In FIG. 2, balloon catheter 200 is illustrated with balloon 201 in an expanded state.

Catheter shaft 226 has an outer tubular member 238 and an inner tubular member 240 disposed within outer tubular member 238, and defining along wit outer tubular member 238, inflation lumen 242. Inflation lumen 242 is in fluid communication with the interior (not shown) of cutting balloon 201. The distal extremity 210 of cutting balloon 201 is sealingly secured to the distal extremity of inner tubular member 240 and the proximal extremity 212 of the balloon 201 is sealingly secured to the distal extremity of the outer tubular member 238. Balloon 201 can be inflated by any fluid, e.g., radiopaque, injected through inflation port 248, or otherwise provided through inflation lumen 242, or by other means, such as from a passageway formed between the outside of the catheter shaft and the member forming balloon 201, depending on the particular design of the catheter. The details and mechanics of fluid transfer and introduction within balloons vary according to the specific design of the catheter, and are well know in the art.

Inner tubular member 240 has an inner lumen 244 extending therethrough and connected with the exterior of outer tubular member 238 via ports 246. Inner lumen 244 can slidably receive a guidewire 234 suitable for advancement through a patient's bodily lumen (not shown) as well as conductors 236 to provide conductors 236 in operative disposition relative to transducers 250.

Although two conductors 236 are shown, it is noted that any number of conductors can be provided in order to supply energy as provided by a power source (not shown) to any number of transducers 250 and then to microscalpel 220. Furthermore, although conductors 236 are shown extending through inner lumen 244, conductors 236 may be provided in operative disposition relative to microscalpel cutting blades 220 in any fashion. For exemplary purposes only, such configurations might include, but are not limited to, conductors 236 extending through inflation lumen 242, or extending through an additional lumen, as may be provided within catheter shaft 226 by providing an additional tubular member within outer tubular member 238.

Ultrasonic transducers 250 are fixedly positioned on outer surface 204 of cutting balloon 201 and extend in a generally parallel fashion along the longitudinal axis thereof. Transducers 250 are operatively disposed relative to microscalpel blades 220, more particularly, microscalpel blades are mounted on top of transducers 250. Microscalpel blades 220 and transducers 250 may be so disposed by any known connection method, such as by the use of conventional adhesives or by non-adhesive based techniques, such as fusion bonding.

As but one example of an alternative configuration within the scope of the present invention, conductors 236 may be ultrasonic transmission elements, which may be operatively attached, at a distal end thereof, directly to microscalpel blades 220. In such a configuration, transducers 250 could be operatively disposed at the proximal ends of conductors 236. As such, the ultrasonic vibrations may be transmitted by the conductors 236 to the microscalpel blades 220 thereby ultrasonically activating the same.

In those embodiments of the invention where ultrasonic energy microscapels 220 are provided with conductors 236, conductors 236 are preferably formed from a metal alloy or other material which exhibits superelastic properties within the range of operating temperature that is normally encountered by the conductors 236 during use. In particular, one preferred superelastic metal alloy of which the conductors 236 may be formed is a nickel-titanium alloy wire made up of 55.8 weight percent nickel (NiTi containing 55.8 weight percent nickel and the balance as titanium). It is understood that the conductors 236, when used as ultrasonic transmission elements, may be tapered, narrowed, or otherwise reduced or changed in cross-sectional dimension so as to decrease the rigidity of the conductors 236 and/or to cause amplification of the ultrasound transmitted to and from a distal end thereof.

The inventive balloon catheter, including at least one microscalpel cutting blade that may optionally be ultrasonically activatable, provides many advantages when used to perform a cutting dilation. Firstly, due at least in part to the small size and enhanced sharpness of the microscalpels and at least in part to the ability to activate the microscalpels with a form of energy, the cutting balloon, when inflated, is capable of creating much sharper and cleaner incisions in a stenosis than a balloon including conventional cutting blades. The ability to selectively activate, deactivate, pulse, or otherwise vary, e.g., as by varying the frequency or amplitude of an oscillatory power source, the source of energy further enhances the cutting precision that can be seen when utilizing the inventive balloon catheter in a treatment. As a result of these advantages, the inventive cutting balloons and balloon catheters can be used to incise stenosis at lower dilatation pressures, or to incise stenosis that are difficult to incise utilizing conventional cutting balloons. As such, trauma to the vessel wall, as well as any subsequent restenosis that can result therefrom, can be reduced.

Figure 3:
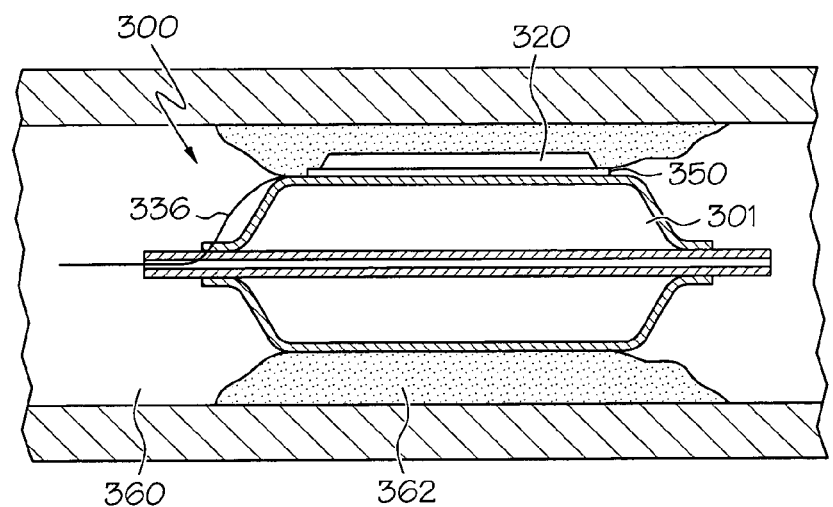
FIG. 3 is a schematic view, in partial cross-section, of the balloon catheter device of FIG. 2, showing in particular the balloon catheter device positioned within a bodily lumen, and wherein the balloon has been inflated so that at least one microscalpel can at least partially incise a stenosis.

In this regard, the present invention further provides a method of dilating and incising a stenosis using the inventive balloon catheter, which method can generally be described with reference to FIG. 3. Generally, the method comprises the steps of providing a balloon catheter 300, wherein the balloon catheter 300 comprises at least a cutting balloon 301 including at least one microscalpel blade 320, which may further optionally be operatively disposed relative to a power source (not shown) so that the microscalpels 320 may be activated thereby. The balloon catheter may be inserted within a bodily lumen 360, as by advancing the catheter over a guide wire (not shown) placed prior to the insertion of the catheter 300, and advanced to the desired treatment site, which is illustrated as stenosis 362. The balloon 301 may then be inflated to cause the radial expansion thereof so that at least a portion of at least one of the microscalpel blades 320 contacts the stenosis 362 thereby at least partially incising the stenosis 362. If desired, during any portion of the inflation or any other period that any portion of microscalpel 320 is disposed within stenosis 362 so as to be capable of incising stenosis 362, microscalpel 320 may be activated with ultrasonic energy as provide to microscalpel 320 by transducer 350 and/or conductor 336. The balloon may then be deflated and withdrawn from the lumen.

The present invention provides apparatus and methods for the treatment of luminal conditions and diseases of body systems including the vascular, pulmonary, lymphatic, and urinary, as well as other body systems that include one or more body lumens. In particular, the present invention provides balloon catheters that may be advantageously utilized for the treatment of diseases of the coronary and peripheral vasculature. Specific conditions generally include coronary and peripheral arterial disease and thrombosis. Such catheters advantageously provide treatment by generally non-invasive techniques by permitting manipulation of distal features of such catheters from their proximal ends.

Numerous characteristics and advantages of the invention meant to be described by this document have been set forth in the foregoing description. It is to be understood, however, that while particular forms or embodiments of the invention have been illustrated, various modifications, including modifications to shape, and arrangement of parts, and the like, can be made without departing from the spirit and scope of the invention.

What is claimed is:

1. A cutting dilation balloon comprising:
   a balloon body having an outer surface;
   at least one ultrasonic microscalpel operatively disposed relative to the outer surface of the body, at least a portion of the at least one microscalpel including a coating comprising a thin-film transducer; and
   a source of power, the at least one microscalpel being operatively disposed relative to the source of power so as to be controllably activatable, the power source being a source of ultrasonic energy and providing oscillatory, thermal, RF, electric energy, or a combination of these, to the at least one microscalpel, the at least one microscalpel being ultrasonically activatable by the provision of the thin film transducer.

2. The cutting dilation balloon of claim 1, wherein the microscalpel comprises a crystalline material.

3. The cutting dilation balloon of claim 2, wherein the crystalline material comprises a monocrystalline material.

4. The cutting dilation balloon of claim 3, wherein the monocrystalline material is silicon.

5. The cutting dilation balloon of claim 1, wherein the microscalpel has a radius of curvature of between about 0.5 nm and about 100 nm.

6. The cutting dilation balloon of claim 1, wherein the microscalpel has a radius of curvature between about 1 nm and about 50 nm.

7. The cutting dilation balloon of claim 1, wherein the thin-film coating comprises silicon dioxide, silicon nitride, titanium diboride, diamond like carbon, silicon carbide or combinations thereof.

8. The cutting dilation balloon of claim 1, wherein the power source is capable of being controlled so as to controllably activate, deactivate, pulse, or otherwise vary the power supplied to the microscalpel.

9. The cutting dilation balloon of claim 1, wherein the thin-film transducer includes at least one piezoelectric material.

10. The cutting dilation balloon of claim 1, wherein the transducer oscillates at a frequency in the range from about 1 kHz to about 300 kHz.

11. The cutting dilation balloon of claim 10, wherein the transducer oscillates at a frequency in the range from about 20 kHz to about 80 kHz.

12. A cutting balloon catheter comprising:
   an elongated catheter shaft having a proximal end, a distal end, and an inflation lumen extending through at least a section thereof;
   a cutting dilation balloon comprising
      a balloon body having an outer surface and an interior in fluid communication with the inflation lumen;
   at least one ultrasonic microscalpel operatively disposed relative to the out surface of the body, at least a portion of the at least one microscalpel including a coating comprising a thin-film transducer; and
   a source of power, the at least one microscalpel being operatively disposed relative to the source of power so as to be controllably activatable, the power source being a source of ultrasonic energy and providing oscillatory, thermal, RF, electric energy, or a combination of these, to the at least one microscalpel, the at least one microscalpel being ultrasonically activatable by the provision of the thin film transducer.

13. The cutting balloon catheter of claim 12, wherein the power source is capable of being controlled so as to controllably activate, deactivate, pulse, or otherwise vary the power supplied to the microscalpel.

14. A method for incising a stenosis comprising the steps of:
   providing a balloon catheter, comprising:
   an elongated catheter shaft having an inflation lumen extending through at least a portion thereof;
   a balloon having an interior, an outer surface, and at least one ultrasonic microscalpel operatively disposed on the outer surface, wherein the interior of the balloon is in fluid communication with the inflation lumen, at least a portion of the at least one ultrasonic microscalpel including a coating comprising a thin-film transducer,
   a source of power, the at least one microscalpel being operatively disposed relative to the source of power so as to be controllably activatable, the power source being a source of ultrasonic energy and providing oscillatory, thermal, RF, electric enemy, or a combination of these, to the at least one microscalpel, the at least one microscalpel being ultrasonically activatable by the provision of the thin film transducer;

inserting the balloon catheter into the bodily lumen and directing the balloon to the site to be dilated; and inflating the balloon so that at least one microscalpel at least partially incises the stenosis.

15. The method of claim 14, wherein the power source is capable of being controlled so as to controllably activate, deactivate, pulse, or otherwise vary the power supplied to the microscalpel.

16. The method of claim 14 wherein the microscalpel is activated with ultrasonic energy for at least a portion of the time that the balloon is inflated.

* * * * *